United States Patent [19]

Sauers

[11] 4,150,122
[45] Apr. 17, 1979

[54] SUBSTITUTED CARBAMATES

[75] Inventor: Richard F. Sauers, Hockessin, Del.

[73] Assignee: E. I. Du Pont de Nemours and Company, Wilmington, Del.

[21] Appl. No.: 867,119

[22] Filed: Jan. 5, 1978

[51] Int. Cl.$^2$ ............................ A01N 9/00; C07F 7/02
[52] U.S. Cl. ................................ 424/184; 260/239 E; 260/326.43; 260/448.2 E; 260/448.2 N; 546/14
[58] Field of Search ................. 424/184; 260/448.2 N

[56] References Cited

U.S. PATENT DOCUMENTS 3,530,220  9/1970  Buchanan ............................ 424/320

Primary Examiner—Allen J. Robinson

[57] ABSTRACT

Insecticidal and nematicidal carbamates, such as methyl 2-dimethylamino-N-{[N-methyl-N-(trimethylsilanyl)-amino]carbonyloxy}-2-oxo-ethanimidothioate, for control of pestiferous insects belonging to such orders as Homoptera, Coleoptera and Diptera.

12 Claims, No Drawings

SUBSTITUTED CARBAMATES

BACKGROUND OF THE INVENTION

This invention relates to insecticidal carbamates.
U.S. Pat. Nos. 3,530,220 and 3,658,870 disclose insecticides such as oxamyl:

$$(CH_3)_2N-\overset{O}{\overset{\|}{C}}-\underset{SCH_3}{\overset{}{C}}=NO\overset{O}{\overset{\|}{C}}-NH-CH_3$$

German Pat. No. 2208329 (1972) discloses trialkylsilylamino-s-triazines as herbicides:

[structure: triazine ring with $R_1$ at top carbon, $R_2NH$ on one carbon, $NHSiR_3$ on the other]

wherein
$R_1$ is cyano, azido, halo, alkoxy or alkylthio;
$R_2$ is alkyl, alkenyl, alkinyl, cycloalkyl, alkoxyalkyl, cyanoalkyl, alkoxycycloalkyl or cyanocycloalkyl;
$R_3$ is alkyl.

SUMMARY OF THE INVENTION

This invention relates to compounds of Formula I, to insecticidal and nematicidal compositions containing them and to the method of using these compounds as insecticides and nematicides:

$$\underset{R_2}{\overset{R_1}{\diagdown}}N-\overset{O}{\overset{\|}{C}}-\underset{SR_3}{\overset{}{C}}=N-O\overset{O}{\overset{\|}{C}}N-\underset{R_5}{\overset{R_4}{\overset{|}{Si}}}-R_6 \quad (I)$$

wherein
$R_1$ and $R_2$ are the same or different, alkyl of 1–4 carbons, methoxy, cycloalkyl of 3–5 carbons, or $-SiR_5R_6R_7$, and $R_1$ and $R_2$ taken together are alkylene of 2–6 carbons; provided that $R_1$ and $R_2$ never total more than 7 carbon atoms and cannot both be cycloalkyl, methoxy or $-SiR_5R_6R_7$;
$R_3$ is alkyl of 1–3 carbons, either branched or straight chain;
$R_4$ is H or $CH_3$;
$R_5$ is alkyl of 1–4 carbons, either branched or straight chain, or phenyl; and
$R_6$ and $R_7$ are independently alkyl of 1–4 carbons, either branched or straight chain.

DESCRIPTION OF THE PREFERRED EMBODIMENTS

Compounds which are preferred for their high insecticidal and nematicidal activity or favorable cost or both are those compounds of Formula I
wherein
$R_1$, $R_2$ and $R_3$ are $CH_3$;
$R_5$ is alkyl of 1–4 carbons, either branched or straight chain; and
$R_6$ and $R_7$ are independently methyl or ethyl.

Specifically preferred for its outstanding insecticidal and nematicidal activity or highly favorable cost or both is methyl 2-dimethylamino-N-{[N-methyl-N-(trimethylsilanyl)-amino]carbonyloxy}-2-oxo-ethanimidothioate having the formula:

$$(CH_3)_2N-\overset{O}{\overset{\|}{C}}-\underset{SCH_3}{\overset{}{C}}=NO\overset{O}{\overset{\|}{C}}\underset{CH_3}{\overset{}{N}}Si(CH_3)_3$$

Preparation

The compounds of Formula I can be prepared, as shown in Equation A, by reacting at least one mole of a substituted 1-(carbamoyl)-N-(carbamoyloxy)thioformimidate of Formula II with one mole of a trisubstituted halosilane of Formula III in the presence of base:

Equation A $$\underset{R_2}{\overset{R_1}{\diagdown}}NC-\underset{SR_3}{\overset{O}{\overset{\|}{C}}}=NO\overset{O}{\overset{\|}{C}}-NH + X-\underset{R_5}{\overset{R_7}{\overset{|}{Si}}}-R_6 \xrightarrow{\text{(base)}}$$

$$\text{(II)} \qquad \text{(III)}$$

$$\underset{R_2}{\overset{R_1}{\diagdown}}NC-\underset{SR_3}{\overset{O}{\overset{\|}{C}}}=NO\overset{O}{\overset{\|}{C}}N-\underset{R_5}{\overset{R_4}{\overset{|}{Si}}}-R_6 + HX$$

$$\text{(I)}$$

wherein
each of $R_1-R_7$ is as previously defined and X is halogen.

The reaction can be carried out in any inert organic solvent, e.g. methylene chloride, dioxane, tetrahydrofuran, chloroform, 1,2-dichloroethane, acetonitrile, benzene, toluene, the xylenes, etc. Mixtures of these solvents can also be used.

Any organic or inorganic base which will function as an acid acceptor can be used in synthesizing the compounds of this invention, e.g. pyridine, trialkylamines such as trimethylamine and triethylamine, N,N-dimethylaniline, the hydroxides, carbonates and bicarbonates of the alkali metals and alkaline earths, and the alkoxides of the alkali metals, such as sodium methoxide and potassium tert-butoxide.

The process can be carried out at a temperature of between about $-20°$ and $60°$ C., preferably between about $-5°$ and $40°$ C. Pressure is not critical, for convenience atmospheric pressure is preferred.

The starting materials (II) can be prepared as described in U.S. Pat. Nos. 3,557,190 and 3,530,220.

In the starting materials of Formula III, chlorides are the preferred halogen for economic reasons, however, bromides, iodides and fluorides may be used. Compounds of Formula III can be prepared by a suitable modification of the methods described in *Organosilicon Compounds*, C. Eaborn, Academic Press, Inc., New York, N.Y. (1960), pages 167–193.

Other routes for preparing compounds of this invention may be used, e.g.:

$$\underset{R_2}{\overset{R_1}{\diagdown}}NC-\underset{SR_3}{\overset{O}{\overset{\|}{C}}}=NOH + R_6-\underset{R_5}{\overset{R_7}{\overset{|}{Si}}}NCO \longrightarrow$$

TABLE I $$R_1\!\!\diagdown\!\!\underset{R_2}{\overset{\phantom{N}}{N}}\!\!-\!\!\overset{O}{\overset{\|}{C}}\!\!-\!\!\underset{SR_3}{C}\!\!=\!\!N\!-\!\!O\!\!-\!\!\overset{O}{\overset{\|}{C}}\!\!-\!\!\underset{R_4}{N}\!\!-\!\!\underset{R_5}{\overset{R_7}{\overset{|}{Si}}}\!\!-\!\!R_6$$

| R₁ | R₂ | R₃ | R₄ | R₅ | R₆ | R₇ |
|---|---|---|---|---|---|---|
| CH₃ | CH₃ | CH₃ | CH₃ | CH₃CH₂ | CH₃CH₂ | CH₃CH₂ |
| CH₃ | CH₃CH₂CH₂CH₂— | CH₃ | CH₃ | CH₃ | CH₃ | CH₃ |
| CH₃ | CH₃ | CH₃ | CH₃ | (CH₃)₃C | CH₃ | CH₃ |
| CH₃ | CH₃ | (CH₃)₂CH | CH₃ | CH₃ | CH₃ | CH₃ |
| CH₃ | (CH₃)₃Si | CH₃ | CH₃ | CH₃ | CH₃ | CH₃ |
| CH₃ | CH₃ | CH₃ | CH₃ | (CH₃)₂CH | CH₃ | CH₃ |
| CH₃ | CH₃ | CH₃ | CH₃ | C₆H₅ | CH₃ | CH₃ |
| (CH₃)₂CH | (CH₃)₂CH | CH₃ | CH₃ | CH₃ | CH₃ | CH₃ |
| CH₃ | CH₃ | CH₃ | CH₃ | CH₃ | (CH₃)₂CH | (CH₃)₂CH |
| CH₃ | CH₃ | CH₃ | CH₃ | C₆H₅ | CH₃CH₂CH₂ | CH₃ |
| CH₃ | CH₃ | CH₃ | H | CH₃ | CH₃ | CH₃ |
| —CH₂CH₂CH₂CH₂CH₂— | | CH₃ | CH₃ | CH₃ | CH₃ | CH₃ |
| CH₃ | CH₃O— | CH₃ | CH₃ | CH₃ | CH₃ | CH₃ |
| CH₃ | CH₃ | CH₃ | CH₃ | CH₃(CH₂)₃ | CH₃(CH₂)₃ | CH₃)CH₂)₃ |

-continued $$R_1\!\!\diagdown\!\!\underset{R_2}{N}\!\!-\!\!\overset{O}{\overset{\|}{C}}\!\!-\!\!\underset{SR_3}{C}\!\!=\!\!N\!\!-\!\!O\!\!-\!\!C\!\!-\!\!NH\!\!-\!\!\underset{R_5}{\overset{R_7}{\overset{|}{Si}}}\!\!-\!\!R_6 \text{ or}$$

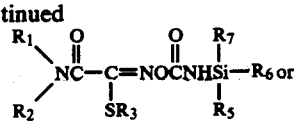

$$R_1\!\!\diagdown\!\!\underset{R_2}{N}\!\!-\!\!\overset{O}{\overset{\|}{C}}\!\!-\!\!\underset{SR_3}{C}\!\!=\!\!NOH + R_6\!\!-\!\!\underset{R_5}{\overset{R_7}{\overset{|}{Si}}}\!\!-\!\!\underset{R_4}{\overset{O}{\overset{\|}{N}}}\!\!-\!\!\overset{O}{\overset{\|}{C}}\!\!Cl \longrightarrow$$

$$R_1\!\!\diagdown\!\!\underset{R_2}{N}\!\!-\!\!\overset{O}{\overset{\|}{C}}\!\!-\!\!\underset{SR_3}{C}\!\!=\!\!N\!\!-\!\!O\!\!-\!\!\overset{O}{\overset{\|}{C}}\!\!-\!\!\underset{R_4}{N}\!\!-\!\!\underset{R_5}{\overset{R_7}{\overset{|}{Si}}}\!\!-\!\!R_6$$

The compounds of Formula I are insoluble in water and generally soluble in most polar organic solvents such as acetone and dimethylformamide.

The following examples further illustrate this invention. Unless otherwise stated, parts and percentages referred to in the examples are by weight and temperatures are in degrees centigrade.

EXAMPLE 1

Methyl 2-dimethylamino-N-{[N-methyl-N)-(trimethylsilanyl)-amino]carbonyloxy}-2-oxo-ethanimidothioate Under a slow nitrogen purge a solution of 11.0 parts of methomyl in 150 parts of THF was cooled to −5°. A solution of 6.8 parts of trimethyl chlorosilane in 10 parts of THF was quickly added to the solution above. Then a solution of 6.3 parts of triethyl amine in 10 parts of THF was added dropwise at −5° to +5° over a 30-minute period. The reaction mixture was allowed to warm to room temperature gradually, then stirred overnight under nitrogen. The NMR spectrum of the resulting oil showed the presence of methyl 2-dimethylamino-N-{[N-methyl-N(trimethylsilanyl)-amino]-carbonyloxy}-2-oxo-ethanimidothioate:

NMR δ (CDCl₃) S 0.3 (S, Me₃Si); 2.5 (S, MeS); 3.0 (S, MeN); 3.2 (d, Me₂N).

By reacting equivalent amounts of other compounds of Formula II with compounds of Formula III using the procedure of Example 1, the compounds of Formula I set forth in Table I can be prepared.

Formulation

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredients(s) and at least one of a) about 0.1% to 20% surfactant(s) and b) about 1% to 99% solid or liquid diluent(s). More specifically, they will contain these ingredients in the approximate proportions set forth in Table II.

TABLE II

| | Percent by Weight | | |
|---|---|---|---|
| | Active Ingredient | Diluent (s) | Surfactant (s) |
| Wettable Powders | 20–90 | 0–74 | 1–10 |
| Oil Suspensions Emulsions, Solutions, (including Emulsifiable Concentrates) | 5–50 | 40–95 | 0–15 |
| Aqueous Suspensions | 10–50 | 40–84 | 1–20 |
| Dust | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers," 2nd Edn., Dorland Books, Caldwell, N.J. The more absorptive diluents are preferred for wettable powders and the denser ones for dusts. Typical liquid diluents and solvents are described in Marsden, "Solvents Guide", 2nd Edn., Interscience, New York, 1950. Solubility under 0.1% is preferred for suspension concentrates; solution concentrates are preferably stable against phase separation at 0° C. McCutcheon Division, MC Publishing Co., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques.

See J. E. Browning, "Agglomeration", *Chemical Engineering*, Dec. 4, 1967, pp. 147ff. and "Perry's Chemical Engineer's Handbook", 4th Edn., McGraw-Hill, N.Y., 1963, pp. 8-59ff.

For further information regarding the art of formulation, see for example:

J. B. Buchanan, U.S. Pat. No. 3,576,834 Apr. 27, 1971, Col. 5, line 36 through Col. 7, line 70 and Exs. 1-4, 17, 106, 123-140.

R. R. Shaffer, U.S. Pat. No. 3,560,616 Feb. 2, 1971, Col. 3, line 48 through Col. 7, line 26 and Exs. 3-9, 11-18.

E. Somers, "Formulation", Chapter 6 in Torgeson, "Fungicides", Vol. I, Academic Press, New York, 1967.

EXAMPLE 2

| Granule | |
|---|---|
| Methyl 2-dimethylamino-N-{[N-methyl-N-(trimethylsilanyl)-amino]carbonyloxy}-2-oxo-ethanimidothioate | 10% |
| Attapulgite granules (low volatile matter, 0.71/0.30 mm; U.S.S.# 25-50 sieves) | 90% |

The active ingredient is warmed to approximately 90° C. and sprayed upon dedusted and pre-warmed attapulgiate granules in a double cone blender. The granules are then allowed to cool and are packaged.

EXAMPLE 3

| Emulsifiable Concentrate | |
|---|---|
| Methyl 2-dimethylamino-N-{[N-methyl-N-(trimethylsilanyl)-amino]carbonyloxy}-2-oxo-ethanimidothioate | 30% |
| Blend of oil soluble sulfonates and polyoxyethylene ester | 4% |
| Xylene | 66% |

The ingredients are combined and stirred with gentle warming to speed solution. A fine screen filter is included in the packaging operation to insure the absence of any extraneous undissolved material in the product.

EXAMPLE 4

| Wettable Powder | |
|---|---|
| Methyl 2-dimethylamino-N-{[N-methyl-N-(trimethylsilanyl)-amino]carbonyloxy}-2-oxo-ethanimidothioate | 40% |
| Dioctyl sodium sulfosuccinate | 1.5% |
| Sodium ligninsulfonate | 3% |
| Low viscosity methyl cellulose | 1.5% |
| Attapulgite | 54% |

The ingredients are thoroughly blended, passed through an air mill, to produce an average particle size under 15 microns, reblended, and sifted through a U.S.S. # 50 sieve (0.3 mm opening) before packaging.

All compounds of the invention may be formulated in the same manner,

Biological Disclosure and Examples

The compounds of this invention are useful for control of insects which are detrimental to agriculture and public health. They readily control pestiferous insects belonging to such orders as Homoptera, Coleoptera and Diptera. More specifically, insects controlled by the compounds of this invention include but are not limited to: house flies (*Musca domestica*), cotton boll weevil (*Anthonomus grandis*), bean aphid (*Aphis fahae*), Mexican bean beetle (*Epilachna varivestis*), and Colorado potato beetle (*Leptinotarsa decemlineata*).

The insects are controlled by applying the material in a convenient formulation to the locus of infestation, to the area to be protected, or to the pests themselves. For the control of insects in agricultural crops, the compound is generally applied to the foliage or other plant parts which are infested or which are to be protected. Effective amounts to be applied depend upon the species to be controlled, its life stage, its size and location, the amount of rainfall, the time of year, moisture, temperature, type of application, and other variables. In general, about 0.1 to about 50 kg/ha may be required for insect control in agriculture with rates of about 0.25 to about 12.5 kg/ha usually being sufficient. Preferred rates in large-scale operations are in the range between about 0.5 and about 4 kg/ha. Where penetration of the insect cuticle is needed for activity, addition of an adjuvant which acts as a penetrant may be beneficial.

The compounds of this invention are also useful for control of nematodes detrimental to agriculture. They readily control but are not limited to the root-knot nematode, *Meloidogyne incognita*. These plant parasitic nematodes are controlled by applying the material in a convenient formulation to infested soil prior to planting. Rates of about 0.25 to about 50 kilograms per hectare are most preferred.

Other methods of applying the compound include: spraying above ground parts of plants such as stems, leaves or buds in which nematodes are present or where later attack is possible; dipping or soaking reproductive parts such as seeds, slips or bulbs. Rates of active ingredient in the sprays or dips are in the range between about 30 grams and about 1.2 kilograms per 100 liters.

The compounds of this invention will generally be used in formulation with a carrier that commonly will consist of oil or water. Applications may be made by use of concentrated or dilute solutions or suspensions comprising the compound of this invention in the carrier. Low-volume applications utilizing suspensions containing 18.75% of the active ingredient may be preferred by some applicators, while others may prefer dilute solutions or suspensions containing only 75 ppm in high-volume applications.

The compounds of this invention can be mixed with fungicides, bactericides, acaricides, other nematicides, other insecticides, or other biologically active compounds in order to achieve desired results with a minimum expenditure of time, effort and material. Amounts of these biologically active materials added for each part by weight of the compound of this invention may vary from 0.0625 to 25 parts by weight. Suitable agents of this type are well known to those skilled in the art. Some are listed below:

Fungicides
  methyl 2-benzimidazolecarbamate
  tetramethyl thiuram disulfide (thiuram)
  n-dodecylguanidine acetate (dodine)
  manganese ethylenebisdithiocarbamate (maneb)
  1,4-dichloro-2,5-dimethoxybenzene (chloroneb)
  methyl 1-(butylcarbamoyl)-2-benzimidazolecarbamate (benomyl)
  N-trichloromethylthiotetrahydrophthalimide (captan)
  N-trichloromethylthiophthalimide (folpet)
Bactericides
  tribasic copper sulfate
  streptomycin sulfate
Acaricides
  senecioic acid, ester with 2-sec-butyl-4,6-dinitrophenol
  6-methyl-1,3-dithiolo[2,3-B]quinonolin-2-one
  ethyl 4,4'-dichlorobenzilate
  1,1-bis(p-chlorophenyl)-2,2,2-trichloroethane
  bis(pentachloro-2,4-cyclopentadien-1yl)
  tricyclohexyl tinhydroxide
  2,4-dinitro-5',6-bis-trifluoromethyl-2-chlorodiphenylamine
Nematicides
  S-methyl 1-(dimethylcarbamoyl)-N-(methylcarbamoyloxy)-thioformimidate
  S-methyl 1-carbamoyl-N-(methylcarbamoyloxy)thioformimidate
  N-isopropylphosphoramidic acid, O-ethyl-O'-[4-(methylthio)-m-tolyl]diester
Insecticides
  3-hydroxy-N-methylcrotonamide (dimethylphosphate)-ester
  methylcarbamic acid, ester with 2,3-dihydro-2,2-dimethyl-7-benzofuranol
  O-[2,4,5-trichloro-α-(chloromethyl)benzylphosphoric acid], O',O'-dimethyl ester
  2-mercaptosuccinic acid, diethyl ester, S-ester with thionophosphoric acid, dimethyl ester
  phosphorothioic acid, O,O-dimethyl, O-p-nitrophenyl ester (methyl parathion)
  methylcarbamic acid, ester with α-naphthol
  methyl O-(methylcarbamoyl)thiolacetohydroxamate (methomyl)
  N'-(4-chloro-o-tolyl)-N,N-dimethylformamidine
  O,O-diethyl-O-(2-isopropyl-4-methyl-6-pyrimidyl-phosphorothioate
I. phosphorothiolothionic acid, O-ethyl-O-[4-methylthio) phenyl]-S-propyl ester
  benzeneacetic acid, 4-chloro-α-(1-methylethyl) [1-cyano-1-(3-phenoxyphenyl)methyl]ester
  phosphorothiolic acid, O-(4-bromo-2-chlorophenyl) O-ethyl-S-propyl ester
  cyclopropanecarboxylic acid, 3-(2,2-dichloroethenyl)-2,2-dimethyl-3-phenoxyphenylmethyl ester The following examples illustrate the insecticidal qualities of the compounds of this invention.

EXAMPLE 5

Twenty adult houseflies were confined in each of several cylindrical stainless steel cages (7.5 cm diameter × 4 cm high) with wire screens at the ends. These were sprayed with acetone solutions of methyl 2-dimethylamino-N-{[N-methyl-N-(trimethylsilanyl)-amino]-carbonyloxy}-2-oxo-ethanimidothioate. Evaluations with respect to % kill were made and are set forth below.

| % Spray Concentration | 24 Hrs. Evaluation % Kill |
|---|---|
| .2 | 100 |
| .05 | 100 |
| Untreated Control | 0 |

EXAMPLE 6

Red kidney bean plants in the two leaf stage were sprayed to run-off with 0.05% suspension of methyl 2-dimethylamino-N-{[N-methyl-N-(trimethylsilanyl)-amino]-carbonyloxy}-2-oxo-ethanimidothioate, the product prepared in accordance with Example 1. Suspensions were made by dissolving 50 mg of that compound in 10 ml of acetone, adding 1 ml of 1% METHOCEL A15 [methylcellulose ether having viscosity of 13–19 cps (2% in water at 20° C.) and a methoxyl content of 27.5–31.5 (audit basis, ASTM D1347)] and diluting to volume with DUPONOL ® ME dry (technical grade sodium lauryl sulfate):water at 1:3000. The plants are held for 48 hours, then caged, each with 10 cotton boll weevil adults. Evaluations with respect to % kill, made 24 hours later, are summarized below.

| % Spray Concentration | 24 Hrs. Evaluation % Kill |
|---|---|
| .05 | 100 |
| Untreated Control | 0 |

EXAMPLE 7

Stems of nasturtium leaves, infested with bean aphids, were placed in individual vials of water. The leaves were sprayed to run-off with a series of suspensions of methyl 2-dimethylamino-N-{[N-methyl-N-(trimethylsilanyl)-amino]carbonyloxy}-2-oxo-ethanimidothioate, prepared in accordance with Example 1. Suspensions were prepared by dissolving 50 mg of that compound in 10 ml of acetone, adding 1 ml of 1% METHOCEL A15 and diluting to volume with DUPONOL ® ME dry: water at 1:3000. Evaluations with respect to % kill 24 hrs. later are set forth below.

| % Spray Concentration | 24 Hrs. Evaluation % Kill |
|---|---|
| .002 | 99 |
| .001 | 73 |
| Untreated Control | 0 |

The following examples illustrate the nematicidal qualities of the compounds of this invention.

EXAMPLE 8

Methyl 2-dimethylamino-N-[N-methyl-N-(trimethylsilanyl)-amino]carbonyloxy-2-oxo-ethanimidothioate, the product prepared in accordance with Example 1, was mixed into soil containing the root-knot nematode, *Meloidogyne incognita*, and the soil was planted with cucumber seeds. After two weeks, the roots were examined for nematode injury and the results are summarized below.

| kg/ha | % Nematode Control |
|---|---|
| 10 | 100 |
| 3 | 100 |
| 1 | 100 |
| 0.5 | 87 |
| Untreated Control | 0 |

EXAMPLE 9

Methyl 2-dimethylamino-N-{[N-methyl-N-(trimethylsilanyl)-amino]carbonyloxy}-2-oxo-ethanimidothioate, prepared in accordance with Example 1, was sprayed on the foliage of tomato plants growing in pots. The soil was covered during the spraying operation to prevent the chemical from coming in contact with the soil. Twenty-four hours after spraying, the soil was inoculated with the root-knot nematode, *Meloidogyne incognita*. The plants were then grown in the greenhouse, taking care not to wet the foliage when watering. Three weeks later, the roots of the plants were examined to see if a foliage application of the chemical had translocated to the roots giving nematode control. The results are tabulated below.

| kg/100 l | % Nematode Control |
|---|---|
| 0.48 | 88 |
| 0.24 | 55 |
| Untreated Control | 0 |

What is claimed is:

1. A compound having the formula:

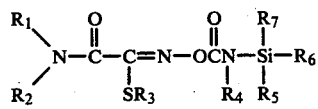

wherein
$R_1$ and $R_2$ are the same or different, alkyl of 1-4 carbons, methoxy, cycloalkyl of 3-5 carbons, or $-SiR_5R_6R_7$;
$R_3$ is alkyl of 1-3 carbons, either branched or straight chain;
$R_4$ is H or $CH_3$;
$R_5$ is alkyl of 1-4 carbons, either branched or straight chain, or phenyl; and
$R_6$ and $R_7$ are independently alkyl of 1-4 carbons, either branched or straight chain.

2. A compound of claim 1
wherein
$R_1$, $R_2$ and $R_3$ are $CH_3$;
$R_5$ is alkyl of 1-4 carbons, either branched or straight chain; and
$R_6$ and $R_7$ are independently methyl or ethyl.

3. A compound of claim 2 which is methyl 2-dimethyl-amino-N-{[N-methyl-N-(trimethylsilanyl)-amino]-carbonyloxy}-2-oxo-ethanimidothioate, having the formula:

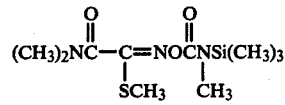

4. A composition suitable for control of pestiferous insects or nematodes consisting essentially of an insecticidally or nematicidally effective amount of a compound of claim 1 and at least one of (a) an inert diluent and (b) a surfactant.

5. A composition suitable for control of pestiferous insects or nematodes consisting essentially of an insecticidally or nematicidally effective amount of a compound of claim 2 and at least one of (a) an inert diluent and (b) a surfactant.

6. A composition suitable for control of pestiferous insects or nematodes consisting essentially of an insecticidally or nematicidally effective amount of the compound of claim 3 and at least one of (a) an inert diluent and (b) a surfactant.

7. A method for control of pestiferous insects which comprises applying to a locus of infestation, to the area of the plant to be protected or to the pests themselves, an insecticidally effective amount of a compound of claim 1.

8. A method for control of pestiferous insects which comprises applying to a locus of infestation, to the area of the plant to be protected or to the pests themselves, an insecticidally effective amount of a compound of claim 2.

9. A method for control of pestiferous insects which comprises applying to a locus of infestation, to the area of the plant to be protected or to the pests themselves, an insecticidally effective amount of the compound of claim 3.

10. A method for control of pestiferous nematodes which comprises applying to said nematodes, a nematicidally effective amount of a compound of claim 1.

11. A method for control of pestiferous nematodes which comprises applying to said nematodes, a nematicidally effective amount of a compound of claim 2.

12. A method for control of pestiferous nematodes which comprises applying to said nematodes, a nematicidally effective amount of the compound of claim 3.

* * * * *